United States Patent [19]

Winn et al.

[11] Patent Number: 4,665,095

[45] Date of Patent: May 12, 1987

[54] USE OF 2-[(3,5-DIHALO-4-AMINOBENZYL)-]IMIDAZOLINES TO STIMULATE ALPHA-1 ADRENERGIC RECEPTORS AND TO TREAT NASAL CONGESTION

[75] Inventors: Martin Winn, Deerfield; John F. Debernardis, Lake Villa, both of Ill.

[73] Assignee: Abbott Laboratories, North Chicago, Ill.

[21] Appl. No.: 807,921

[22] Filed: Dec. 11, 1985

[51] Int. Cl.$^4$ .................. A61K 31/415; C07D 233/24
[52] U.S. Cl. ..................................... 514/401; 548/347
[58] Field of Search ................. 548/347, 355; 514/401

[56] References Cited

U.S. PATENT DOCUMENTS

| | | | |
|---|---|---|---|
| 2,731,471 | 1/1956 | Synerholm et al. | 548/347 |
| 2,868,802 | 1/1959 | Hueni et al. | 548/347 |
| 3,536,712 | 10/1970 | Keck et al. | 546/229 |
| 3,660,423 | 5/1972 | Wysong et al. | 548/347 |
| 4,461,914 | 7/1984 | Bentley | 564/357 |
| 4,506,074 | 3/1985 | Huff et al. | 546/278 |

OTHER PUBLICATIONS

Burger, *Medicinal Chemistry*, 2nd Ed., pp. 72-77 1960.
Porsolt et al., Eur. J. Pharmac., 47, pp. 379-391, (1978).
Porsolt et al., Arch. Int. Pharmacodyn., 229, pp. 327-336 (1977).
Jesberger et al., Biol. Psychiatry, 20, pp. 764-784 (1985).
Willner, Psychopharmacology, 83, pp. 1-16 (1984).
Kelwala et al., J. Clin. Psychiatry, 44 (5), pp. 40-48 (1983).
Peet et al., Br. J. Clin. Pharmac., 5, pp. 55-95 (1978).

*Primary Examiner*—John M. Ford
*Assistant Examiner*—Kurt G. Briscoe
*Attorney, Agent, or Firm*—Steven F. Weinstock; Martin L. Katz

[57] ABSTRACT

Disclosed herein are alpha adrenergic and nasal decongestant compounds of the formula

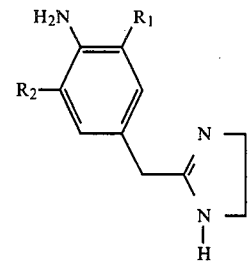

wherein $R_1$ and $R_2$, each being the same or different, are halogens, and the pharmaceutically acceptable salts thereof.

4 Claims, No Drawings

USE OF 2-[(3,5-DIHALO-4-AMINOBENZYL)]IMIDAZO-LINES TO STIMULATE ALPHA-1 ADRENERGIC RECEPTORS AND TO TREAT NASAL CONGESTION

TECHNICAL FIELD

The present invention relates to novel compounds, compositions and methods of using the compounds as adrenergic agents and for the treatment of nasal congestion.

BACKGROUND ART

Nasal congestion is characteristic of several diseases including the common cold, allergic rhinitis, sinusitis and hay fever. Nasal congestion is caused by dilation of the blood vessels of the nasal mucosa, which leads to swelling of the tissue lining the nasal cavity. The blood vessels of the nasal mucosa are rich in adrenergic receptors. Among the commonly used topical nasal decongestants that act by adrenergic stimulation are the imidazoline derivatives naphazoline, oxymetazoline, xylometazoline and tetrahydrozoline. These adrenergic stimulants constrict the blood vessels in the nasal mucosa and thus relieve the swelling of the nasal tissues.

A number of side effects are associated with use of these agents. For example, oxymetazoline and naphazoline often cause irritation of the nasal mucosa. Excessive or prolonged use of topical nasal decongestants may cause rebound congestion or rhinitis medicamentosa. Rebound congestion or rhinitis medicamentosa is a condition whereby congestion is reduced initially but is followed by a rebound of greater nasal stuffiness that is not relieved when further doses of decongestant are administered. Further, if the topical decongestants are systematically absorbed, side effects may include insomnia, headache, nausea, irritability, dizziness, perspiration, hypertension, tachycardia, palpitations and cardiac arrhythmias.

Thus, a compound with good topical decongestant activity and reduced potential for nasal irritation and other side effects is desirable.

DISCLOSURE OF THE INVENTION

Compounds of the formula

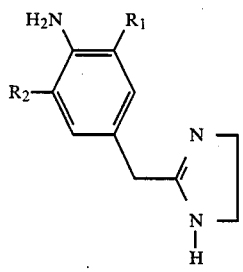

wherein $R_1$ and $R_2$, each being the same or different, are Cl, Br, I or F; and its pharmaceutically acceptable salts are alpha-1 adrenergic receptor stimulants and alpha-2 adrenergic receptor inhibitors and are also nasal decongestants. These compounds exhibit a combination of alpha-1 adrenergic receptor agonist and alpha-2 adrenergic receptor antagonist activity and have no alpha-2 adrenergic receptor agonist activity. When administered intranasally as a spray or topical solution, relief of nasal congestion is observed, while undesirable side effects are reduced or eliminated.

Pharmaceutically acceptable salts of the compounds of this invention include, but are not limited to, non-toxic acid addition salts with inorganic acids such as hydrochloric, hydrobromic, sulfuric, boric or phosphoric acid, or with organic acids such as acetic, oxalic, valeric, oleic, palmitic, stearic, lauric, benzoic, fumaric, succicnic, maleic, malic, tartaric or citric acid, or with organic sulfonic acids such as methanesulfonic or p-toluenesulfonic acid. The compounds of the invention can be administered in any effective pharmaceutically acceptable form, e.g., in oral, parenteral or infusable dosage forms, or intranasal dosage forms. Suitable parenteral routes of administration include, for example, intramuscular, intravenous, intraperitoneal or subcutaneous administration of the compounds.

In addition to the active compounds, compositions according to this invention for parenteral injection may comprise pharmaceutically acceptable sterile aqueous or nonaqueous solutions, suspensions, aerosols or emulsions. Examples of suitable nonaqueous carriers, diluents, solvents or vehicles include propylene glycol, polyethylene glycol, vegetable oils, such as olive oil, and injectable organic esters such as ethyl oleate. Such compositions may also contain adjuvants such as preserving, wetting, emulsifying, and dispersing agents. They may be sterilized, for example, by filtration through a bacteria-retaining filter, or by incorporating sterilizing agents into the compositions. They can also be manufactured in the form of sterile solid compositions which can be dissolved in sterile water, or other sterile injectable medium, immediately before use.

Solid dosage forms for oral administration include capsules, tablets, pills, powders and granules. In such solid dosage forms, the active compound may be admixed with at least one inert diluent such as sucrose, lactose or starch. Such dosage forms may also comprise, as is normal practice, additional substances other than inert diluents, e.g., lubricating agents such as magnesium stearate. In the case of tablets, capsules and pills, the dosage forms may also comprise buffering agents. Tablets and pills can additionally be prepared with enteric coatings.

Liquid dosage forms for oral administration include pharmaceutically acceptable emulsions, solutions, suspensions, syrups and elixirs containing inert diluents commonly used in the art, such as water. Besides such inert diluents, compositions may also comprise adjuvants, such as wetting agents, emulsifying and suspending-agents, and sweetening, flavoring and perfuming agents.

Dosage forms for intranasal administration include solutions, suspensions or emulsions of the active compound in a liquid medium for administration as drops or a spray. Suitable liquid media include water, propylene glycol and other pharmaceutically acceptable alcohols, and sesame or peanut oil and other pharmaceutically acceptable vegetable oils. Dosage forms for intranasal administration also include solutions, suspensions or emulsions of the active compound in liquid propellants such as dichlorodifluoromethane or chlorotrifluoroethane for administration from a pressurized container. Dosage forms for intranasal administration may also include ointments or gels containing the active compound. The dosage forms for intranasal administration may be sterilized and/or may contain adjuvants such as preservatives, stabilizers, emulsifiers, salts for varying the osmotic pressure, or buffers.

Dosage levels of the active compound in the compositions of the invention may be varied so as to obtain a desired therapeutic response for a particular composition and method of administration. Generally, the active compound will be administered as an aqueous solution spray of from 0.0001 to 1.0 percent concentration. More preferably the concentration will be from 0.025 to 0.10 percent. If desired the daily dose may be divided into multiple doses for administration.

The foregoing may be better understood from the following examples which are presented for purposes of illustration and are not intended to limit the scope of the inventive concepts.

EXAMPLE 1

3,5-Dichloro-4-amino benzyl alcohol

Methanol (400 ml) was added dropwise over 2 hours to a mixture of methyl-3,5-dichloro-4-aminobenzoate (110 g), $NaBH_4$ (142.5 g) and t-butanol (1.1 L). At the end of the addition, the mixture was refluxed 3 hours, cooled, then $H_2O$ (1.2 L) was carefully added. The resulting layers were separated and the organic phase was washed with $H_2O$ (2×200 mL), separated, dried ($MgSO_4$), filtered and evaporated to afford the desired product (89 g), mp 110–112° C.

EXAMPLE 2

N-(2,6-dichloro-4-chloromethylphenyl) sulfinyl imide 3,5-Dichloro-4-amino benzylalcohol (88 g) was dissolved in dichloroethane (900 mL) and then thionyl chloride (141 g) in dichloroethane (200 mL) was rapidly added, with stirring. An exothermic reaction occurred with the mixture thickening. After about 30 minutes the reaction mixture was no longer viscous and became amber colored. Refluxing, was continued an addition 1 hour, followed by concentration of the reaction solution. This afforded 117 g of the desired product as an oil which solidified in the freezer.

EXAMPLE 3

3,5-Dichloro-4-amino benzylnitrile

The product from Example 2 (125 g) was dissolved in ether (300 mL) and added with stirring to an ice cooled mixture of concentrated HCl (300 mL) and ether (200 mL). A solid resulted which was filtered after 15 minutes and added to an ice cold suspension of powdered NaCN (86 g) in DMSO (430 mL). The mixture was heated to 60° C. and stirred for 45 minutes. The reaction was cooled, ice added, and the solid filtered. The filtered solid was dissolved in $CH_2Cl_2$ (400 mL), then washed successively with dilute aqueous NaOH and then saturated brine. The organic layer was separated and dried ($MgSO_4$) to afford 67 g of the desired product, mp 117–119° C.

EXAMPLE 4

2-[(3,5-Dichloro-4-aminobenzyl)]imidazoline hydrochloride

The product of Example 3 (10 g) was dissolved in DME (80 mL) and MeOH (9.5 mL). The solution was cooled in an ice bath and HCl (g) was bubbled through the solution for 30 minutes. The reaction flask was stoppered and allowed to stand at room temperature overnight. The solution was concentrated, ether (50 mL) was added, and the resulting solid was filtered. The solid was added to EtOH (80 mL) and the solution was cooled, followed by addition of ethylenediamine (17.8 mL). After stirring for 15 minutes, the solution was refluxed for 15 minutes. The reaction mixture was concentrated and $CHCl_3$ (40 mL) was added, followed by addition of $H_2O$ and aqueous 45% KOH (5 mL). After mixing, the organic layer was separated and washed with $H_2O$ (2×50 mL). The organic layer was again separated and methanolic HCl was added. After drying over $MgSO_4$, evaporation provided a crude product. This was dissolved in $CH_3CN$ (150 mL) and heated on a steam bath for about 3 minutes. The solution was cooled and the resulting crystals were filtered, washed with cold $CH_3CN$ (20 mL) and then ether (20 mL), giving the desired product, mp 261–264° C.

EXAMPLE 5

2-[(3,5-Difluoro-4-amino)benzyl]imidazoline hydrochloride

Starting with methyl-3,5-difluoro-4-amino benzoate and utilizing consecutively the procedures of Examples 1–4, affords the desired compound.

EXAMPLE 6

2-[(3,5-Diiodo-4-amino)benzyl]imidazoline hydrochloride

Starting with methyl-3,5-diiodo-4-amino benzoate and utilizing consecutively the procedures of Examples 1–4, affords the desired compound.

EXAMPLE 7

Alpha-1-Receptor Interaction in Rabbit Aorta a. Method Helical strips of the female rabbit thoracic aorta (4×20 mm) were suspended in 10 ml tissue baths containing bicarbonate buffer of the following composition (mM): NaCl 119, KCl 4.7, $CaCl_2$ 2.5, $MgSO_4$ 1.5, $KH_2PO_4$ 1.2, $NaHCO_3$ 25, dextrose 11, ascorbic acid 0.3, and NaEDTA 0.03. The solution was gassed with 95% $O_2$+5% $CO_2$ at 37° C., pH 7.40. Isometric contractions of the tissues, preloaded to a tension of 2 G were measured with Grass FTO3 strain gauges and recorded on a Grass Model 7 polygraph. Following an equilibration period of 90 minutes, tissues were readjusted to 2 G tension, and a control cumulative dose-response curve was obtained for the standard agonist, norepinephrine. After washout of norepinephrine (60–90 minutes), tissues were again equilibrated and a cumulative dose-response curve of the tested agonist was obtained.

b. Results The product of Example 4, when tested in accordance with method "a", was a full (alpha-1) agonist in rabbit aorta being 1.31 ±0.22 fold more potent than norepinephrine.

EXAMPLE 8

Alpha-2 Receptor Interaction in Phenoxybenzamine (PBZ)-Treated Dog Saphenous Veins a. Method Rings (3–4 mm wide) of lateral saphenous veins excised from beagle dogs of either sex were suspended in 10 ml tissue baths containing bicarbonate buffer of the following composition (mM): NaCl 119, KCl 4.7, $CaCl_2$ 2.5, $MgSO_4$ 1.5, $KH_2PO_4$ 1.2, $NaHCO_3$ 20, dextrose 11, ascorbic acid 0.3, NaEDTA 0.03, cocaine 0.03, hydrocortisone hemisuccinate 0.04, and propranolol 0.004. The solution was gassed with 95%

$O_2 + 5\%$ $CO_2$ at 37° C., pH 7.40. Isometric contractions of the tissues, preloaded with a tension of 2 G were measured with Grass FTO3 strain gauges and recorded on a Grass Model 7 polygraph. Following an equilibration period of 15–20 minutes and maximal contraction by norepinephrine (1E-4M), the tissues were washed for 60 minutes at which time they were exposed to phenoxybenzamine (PBZ, 1E-7M) for 30 minutes. At the end of PBZ treatment a thorough washout followed for 60 minutes. Tissues were then re-adjusted to 2 G tension, and a control cumulative dose-response curve was obtained for the standard agonist, norepinephrine. After washout of norepinephrine (45–60 minutes), tissues were again equilibrated and a cumulative dose-response curve of the tested agonist was obtained. When antagonist is tested in this model, various concentrations of such an agent are administered into the tissue bath 30 minutes prior to the second dose-response curve of norepinephrine. This experiment is replicated in several tissues for each concentration of the test compound or control vehicle. The competitive antagonism is evaluated and characterized using the $pA_2$ (1/affinity) and its slope.

b. Results The product of Example 4, when tested in accordance with method "a", was devoid of any alpha-2 agonistic activity in this tissue up to the concentration of $10^{-3}$ M (n=2). On the other hand, the product of Example 4 exhibited a competitive alpha-2 antagonism of norepinephrine contraction in this tissue ($pA_2 = 6.51 \pm 0.23$; Slope $= 0.93 \pm 0.19$).

EXAMPLE 9

Alpha-1/Alpha-2 Receptor Interactions at Pre-Postsynaptic Receptors of Rabbit Pulmonary Artery a. Method Helical strips of main pulmonary artery (4×30 mm) of female rabbits were mounted vertically between two platinum electrodes to Grass FTO3 strain gauges following 60 minutes of incubation with $^3$H norepinephrine ($0.375 \times 10^{-6}$ M at 11 Ci/mmol). The preparation was then superfused with vehicle buffer of the following composition (mM): NaCl 119, KCl 4.7, $CaCl_2$ 2.5, $MgSO_4$ 1.5, $NACHO_3$ 25, $KH_2PO_4$ 1.2, glucose 11, ascorbic acid 0.3, NaEDTA 0.03, cocaine 0.03, hydrocortisone hemisuccinate 0.04, propranolol 0.004. The solution was gassed with 95% $O_2 + 5\%$ $CO_2$ at 37° C., pH 7.40; and superfused at a constant rate of 2 ml/minute. Electrical field stimulations (2 Hz; 9 V; 0.3 msec; 3 minutes) were applied to the tissues in 48-minute intervals to evoke release of endogenous norepinephrine, reflected by an increase of tritium overflow in the fractional 3-minute collections of superfusate (presynaptic event) and mediating the isometric contraction of the tissue (postsynaptic event).

b. Results In the superfused rabbit pulmonary artery testing, the product of Example 4 exhibited a distinct stimulation of the postsynaptic (alpha-1) receptor at concentrations as low as $10^{-7}$ M.

In the same experiments, on the other hand, the product of Example 4 was devoid of any inhibitory effect on the stimulated overflow (at concentrations up to $10^{-5}$ M), signifying that it did not possess any presynaptic (alpha-2) agonistic activity. In fact, the product of Example 4 potentiated the stimulated tritium overflow (at concentrations $10^{-6}$ M), thus showing again that this compound has alpha-2 antagonistic activity.

EXAMPLE 10

Effect on Airway Resistance in Anesthetized Dogs Following Intranasal Spray Administration a. Method Beagle dogs of either sex, weighing 9–12 kg were anesthetized with nembutal (30 mg/kg, intravenously) with supplemental doses administered throughout the experiment as required. The dogs were intubated with a cuffed endotracheal tube and were ventilated with room air by means of a Harvard respiration pump. Arterial blood pressure was recorded from a femoral artery using a Statham P23Gb pressure transducer. A tachygraphic recording of heart rate was obtained from the blood pressure signal.

A constant flow of air (2 liters/minute); provided by an anesthetic machine (CAECO) was administered into a nasal cavity through a 6 cm long plastic tube tapered to a diameter of 6 mm to fit into the right nostril. The air perfused the nasal cavity and exited through the mouth. The resistance to the air flow exerted by the large surface area of the nasal mucosa was measured as a nasal pressure in cm of water, using Model MP 45 Validyne transducer. For drug administration, a bypass arrangement in the air tubing permitted flow through a 690 Ultrasonic humidifier containing the nebulized drugs. This instrument atomized the drug solution into a vapor which was carried by the air flow into the nasal passages. It was calibrated to nebulize 1.65 ml of fluid over a 5 minute period of perfusion. Since the amount of drug administered in this way is extremely small and not directly measurable, the doses were calculated from the concentration of drug in the humidifier and volume of fluid used in each administration (in mg per dog). The nasal resistance, heart rate and blood pressure were monitored prior to and then 2 hours following the drug administration. A decrease in nasal resistance is indicative of vasoconstrictor activity. The changes in heart rate and blood pressure reflect a systematic absorption of the test compound.

b. Results When tested in accordance with method "a", the product of Example 4 administered in aerosol produced a strong and dose dependent decrease of the resistance to air flow on its passage through the nasal cavity. The threshold dose of the product of Example 4 which produced this effect was 0.00165 mg. An initial transient elevation of this parameter was observed with all doses of all compounds tested, reflecting the manipulation of the nebulizing operation. At the effective nasal decongestant dose, the product of Example 4 was devoid of any systematic hemodynamic effects as might be observed with an alpha agonist. Only the highest tested dose of the product of Example 4 (1.65 mg) produced a slight elevation of the blood pressure, approximately 10% above the base level. This observation suggests that the product of Example 4 might be poorly absorbed from the nasal mucosa and thus unlikely to cause any negative side effects.

EXAMPLE 11

Effect on Nasal Irritation in Rats

The product of Example 4 was dissolved in phosphate buffered normal saline and adjusted to a pH of approximately 7. The solution was prepared at the following concentrations: 0.05, 0.15, 0.5 and 1.5 percent. Groups of five male rats (CD strain) were administered each dose. The rats were approximately 5 weeks old at the start of treatment. Prior to dosing, ketaminehydrochloride was administered intraperitoneally to produce transient anesthesia to facilitate test compound administration. Rats in each group were given 0.04 mL/day of the appropriate solution for 14 days. The dosage was divided equally between both nostrils (i.e., 0.02 mL/nostril/day).

The product of Example 4 caused no nasal mucosal injury or any systemic toxic effects even at its greatest concentration tested, i.e., 1.5%.

In contrast, oxymetazoline, when tested, induced nasal mucosal injury at 0.5% and 1.5% concentration. Systemic side effects and deaths occurred in most animals following repeated administration of these doses, suggesting systemic absorption and toxicity associated with oxymetazoline. Oxymetazoline did not cause any toxicity or nasal injury at 0.05% to 0.15% concentrations.

In summary, the compounds of the invention demonstrate alpha-1 agonist activity, alpha-2 antagonist activity, efficacy as nasal decongestants and no nasal mucosa irritation.

The foregoing is merely illustrative of the invention and is not intended to limit the invention to the disclosed compounds, methods and compositions. For example, the compounds of this invention may also be useful for treating ophthalmic or otic congestion. They also may be used as antidepressants, antihypertensives or inhibitors of platelet aggregation. Other variations and changes which are obvious to one skilled in the art are also intended to be within the scope and nature of the invention which are defined in the appended claims.

What is claimed is:

1. A method for stimulating alpha-1 adrenergic receptors and inhibiting alpha-2 adrenergic receptors comprising administering to a patient in need, a therapeutically effective amount of a compound of the formula

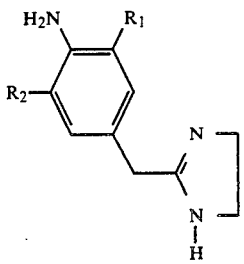

wherein $R_1$ and $R_2$, each being the same or different are halogens; or a pharmaceutically acceptable salt thereof.

2. The method of claim 1 wherein $R_1$ and $R_2$ are Cl.

3. A method of treating nasal congestion comprising administering to a patient in need, a therapeutically effective amount of a compound of the formula

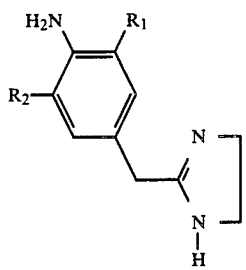

wherein $R_1$ and $R_2$, each being the same or different, are halogens; or a pharmaceutically acceptable salt thereof.

4. The method of claim 3 wherein $R_1$ and $R_2$ are Cl.

* * * * *